United States Patent [19]
Tashiro et al.

[11] Patent Number: 5,589,182
[45] Date of Patent: Dec. 31, 1996

[54] COMPOSITIONS AND METHOD OF TREATING CARDIO-, CEREBRO-VASCULAR AND ALZHEIMER'S DISEASES AND DEPRESSION

[76] Inventors: Renki Tashiro, Asahichyo 2-24-15, Fuchyu, Tokyo, Japan; Ruth H. Pater, 106 Tuckahoe Trace, Yorktown, Va. 23693

[21] Appl. No.: 161,350

[22] Filed: Dec. 6, 1993

[51] Int. Cl.$^6$ .............................. A61K 9/08; A61K 9/14; A61K 9/20; A61K 9/48; A61K 35/78
[52] U.S. Cl. .................. 424/423; 424/195.1; 424/451; 424/464; 424/489; 424/422; 514/824; 514/879
[58] Field of Search ................... 424/195.1, 464, 424/451, 489, 422, 423

[56] References Cited

U.S. PATENT DOCUMENTS

| | | | |
|---|---|---|---|
| 4,042,592 | 8/1977 | Sawa | 260/286 |
| 4,200,629 | 4/1980 | Nakamura | 424/195 |
| 4,339,435 | 7/1982 | Adachi | 424/115 |
| 4,419,349 | 12/1983 | Kojima | 424/195 |
| 4,469,685 | 9/1984 | Kojima | 424/195 |
| 4,528,192 | 7/1985 | Kim | 424/195.1 |
| 4,618,495 | 10/1986 | Okuda et al. | 424/195.1 |
| 4,684,628 | 8/1987 | Liu | 514/26 |
| 4,708,949 | 11/1987 | Liu | 514/26 |
| 4,717,664 | 1/1988 | Hara et al. | 435/133 |
| 4,755,504 | 7/1988 | Liu | 514/26 |
| 4,769,363 | 9/1988 | Misaki | 514/54 |
| 4,795,739 | 1/1989 | Lifson et al. | 514/8 |
| 4,795,742 | 1/1989 | Liu | 514/21 |
| 4,842,859 | 6/1989 | Liu | 424/195.1 |
| 4,843,067 | 6/1989 | Liu | 514/54 |
| 4,869,903 | 9/1989 | Lifson et al. | 424/195.1 |
| 4,886,666 | 12/1989 | Liu | 424/195.1 |
| 4,898,890 | 2/1990 | Sato et al. | 514/685 |
| 4,906,470 | 3/1990 | Liu | 424/195.1 |
| 4,906,471 | 3/1990 | Liu | 424/195.1 |
| 4,966,893 | 10/1990 | Pang et al. | 514/54 |
| 4,999,376 | 3/1991 | Liu | 514/468 |
| 5,055,297 | 10/1991 | Fujimaki et al. | 424/195.1 |
| 5,128,131 | 7/1992 | Motoyama et al. | 424/195.1 |
| 5,135,010 | 8/1992 | Fan | 131/359 |
| 5,137,878 | 8/1992 | Pang et al. | 514/54 |
| 5,162,037 | 11/1992 | Witson-Fischman | 600/12 |
| 5,178,865 | 1/1993 | Ho et al. | 424/195.1 |
| 5,190,757 | 3/1993 | Kim | 424/195.1 |
| 5,204,369 | 4/1993 | Vallee et al. | 514/456 |

*Primary Examiner*—James M. Spear
*Attorney, Agent, or Firm*—Kerkam, Stowell, Kondracki & Clarke; Dennis P. Clarke

[57] ABSTRACT

A pharmaceutical composition suitable for the treatment of a condition selected from the group consisting of cardiovascular disease, cerebrovascular disease, Alzheimer's disease, depression or combinations thereof comprising various mixtures of the aqueous extracts of tissue of specific Chinese plants and herbs. A method of preparing the pharmaceutical compositions of the invention and a method for treating a patient therewith are also disclosed.

35 Claims, 8 Drawing Sheets

COMPOSITIONS AND METHOD OF TREATING CARDIO-, CEREBRO-VASCULAR AND ALZHEIMER'S DISEASES AND DEPRESSION

BACKGROUND OF THE INVENTION

1. Field of the Invention

The present invention relates to a therapeutic composition derived from Chinese herbs and plants.

2. Discussion of the Prior Art

There is a current revival of interest in Chinese folk medicines which are principally derived from Chinese herbs or other types of plants. This interest in Chinese herbs was prompted by Chinese folklore wherein a number of such herbs have been reputed to have anti-infective activity and to be well-tolerated by humans. A subset of these herbs also appears to exhibit anti-HIV activity [Chang et al, *Antiviral Research*, Vol. 9, pages 163–176 (1988); and Chang et al, *Antiviral Research*, Vol. 11, page 263–273 (1989)].

However, Chinese folk medicine is based largely on anecdotal observations spanning the past several thousands of years. Hence, the effectiveness of the medicinal herbs used by folk medicine practitioners has, for the most part, not been substantiated by scientific methods. Despite this lack of scientific proof, it is quite possible that some herbal remedies may have specific therapeutic action, as was proven to be the case with the anti-malarial, qinghaosu, and perhaps even anti-HIV activity [Klayman, *Science*, vol. 228, pages 1049–1055 (1985)]. Consequently, with regard to the possible anti-HIV activity among Chinese herbal extracts, an urgent need exists for: (1) the identification of effective therapeutic herbal extracts, (2) the substantive documentation, by modern scientific methods, of the effectiveness of these herbal extracts against various pathological states, and (3) the identification of effective therapeutic Chinese herbal extracts that are less toxic than the currently available agents.

A plethora of pharmaceutical agents having varying degrees of effectiveness are commonly utilized for the treatment of cerebro- and cardio-vascular diseases. U.S. Patents disclosing Chinese medicines derived from plant materials useful for the treatment of these diseases and their sequela include Nos. 4,906,470; 4,708,949; 4,755,504; 4,795,742; 4,999,376 and 5,128,131. Chinese medicines for the treatment of heart disease are also described in Chinese Patent Nos. CN 1033567; CN 1041279 and CN 87101313.

Treatments for depression presently include the use of anti-depressant drugs, psychotherapy and electro-convulsive therapy. Herbal extracts have also been suggested for the treatment of depression in U.S. Pat. No. 5,162,037.

Despite the intensive research conducted during the last two decades, Alzheimer's disease, which afflicts about four million Americans and causes 100,000 deaths in the U.S. alone each year, remains incurable because of the lack of effective medicines. Recently, tacrine (1,2,3,4-tetrahydro-9-acridinamine) has been suggested for treatment of this disease.

The use of various Chinese herbal derivatives for treating senile dementia of the Alzheimer's type (SDAT) is disclosed in U.S. Pat. Nos. 4,966,893 and 5,137,878.

Other U.S. Patents disclosing various therapeutic properties of Chinese medicines derived from certain Chinese herbs and plants include: 4,042,592; 4,200,629; 4,339,435; 4,419,349; 4,469,685; 4,528,192; 4,618,495; 4,684,628; 4,717,664; 4,769,363; 4,795,739; 4,842,859; 4,843,067; 4,869,903; 4,886,666; 4,898,890; 4,906,471; 5,055,297, 5,178,865; 5,190,757 and 5,204,369.

While the statistics are unknown, it is believed that many people are currently suffering from complications of heart, Alzheimer's and depression diseases. No medication exists that can simultaneously treat all of these three diseases. Moreover, the prior art generally does not have a desired combination of safety, effectiveness and low cost which is needed for treating a large number of patients who have very different medical conditions and socio-economic backgrounds. Accordingly, there is a continuous search in the art for a medicine that is safe, useful and inexpensive for the prevention and treatment of heart, Alzheimer's and depression diseases.

It is an object of the present invention to provide novel pharmaceutical compositions suitable for the treatment of cardiovascular disease, cerebrovascular disease, SDAT and depression derived from specific combinations of Chinese plants.

It is another object of the present invention to provide novel therapeutic methods for treating cardiovascular disease, cerebrovascular disease, SDAT and depression employing medicines derived from certain Chinese plants.

Finally, it is an additional object of the invention to provide novel methods for preparing the above-described medicines from Chinese plants.

SUMMARY OF THE INVENTION

These and other objects are realized by the present invention, one embodiment of which relates to a pharmaceutical composition suitable for the treatment of a condition selected from the group consisting of cardiovascular disease, cerebrovascular disease, Alzheimer's disease, depression or combinations thereof comprising:

I. a mixture of the aqueous extracts of tissue of the plants:
 a. *Asparagus cochinchinensis,*
 b. *Ophiopogon japonicus,*
 c. *Salvia miltiorrhiza,*
 d. *Angelica aeutiloba kitagawa,*
 e. *Rehmannia glutinosa Liboschitz,*
 f. *Poria cocos wolf,*
 g. *Schizandra chinensis,*
 h. *Platycodon grandiflorum,*
 i. *Polygala tenuifolia,*
 j. *Zizyphus jujuba,*
 k. *Biota orientalis,*
 l. *Pueraria pseudo-hirsuta,*
 m. *Panax ginseng,*
 n. *Codonopsis pilosula,*
 o. *Scrophularia ningpoensis,*
 p. *Glycyrrhiza uralensis,*
 q. *Panax pseudo-ginseng,*
 r. *Ganoderma japonicum,*
 s. *Coptis chinensis,*
 t. *Chrysanthemum morifolium,* and
 u. *Phellodendron amurense;*

II. a mixture of the aqueous extracts of tissue of the plants:
 a. *Asparagus cochinchinensis,*
 b. *Ophiopogon japonicus,* c. *Salvia miltiorrhiza,*
d. *Angelica aeutiloba kitagawa,*
e. *Rehmannia glutinosa Liboschitz,*
f. *Poria cocos wolf,*
g. *Schizandra chinensis,*
h. *Platycodon grandiflorum,*
i. *Polygala tenuifolia,*
j. *Zizyphus jujuba,*
k. *Biota orientalis,*
l. *Pueraria pseudo-hirsuta,*
m. *Panax ginseng,*
n. *Codonopsis pilosula,*
o. *Scrophularia ningpoensis,*
p. *Glycyrrhiza uralensis,*
q. *Panax pseudo-ginseng,* and
r. *Ganoderma japonicum;*

III. a mixture of the aqueous extracts of tissue of the plants:

a. *Asparagus cochinchinensis,*
b. *Ophiopogon japonicus,*
c. *Salvia miltiorrhiza,*
d. *Angelica aeutiloba kitagawa,*
e. *Rehmannia glutinosa Liboschitz,*
f. *Poria cocos wolf,*
g. *Schizandra chinensis,*
h. *Platycodon grandiflorum,*
i. *Polygala tenuifolia,*
j. *Zizyphus jujuba,*
k. *Biota orientalis,*
l. *Pueraria pseudo-hirsuta,*
m. *Panax ginseng,*
n. *Scrophularia ningpoensis,*
o. *Glycyrrhiza uralensis,*
p. *Ganoderma japonicum,*
q. *Coptis chinensis,* and
r. *Chrysanthemum morifolium;* or IV. a mixture of finely divided tissue of the plants:

a. *Salvia miltiorrhiza,*
b. *Panax pseudo-ginseng,*
c. *Red ginseng,* and
d. Amber.

A further embodiment of the invention comprises a method of preparing the pharmaceutical compositions I, II or III above by extracting the water-soluble components from the tissue of the plants with an aqueous medium.

Yet another embodiment of the invention concerns a method of preparing the pharmaceutical composition IV above comprising grinding the tissues to a finely divided state.

A final embodiment of the invention relates to a method for treating a patient in need thereof comprising administering thereto a therapeutic amount of the pharmaceutical compositions described above effective to prevent or ameliorate the effects of cardiovascular disease, cerebrovascular disease, Alzheimer's disease, depression or combinations thereof.

DETAILED DESCRIPTION OF THE INVENTION

Although all of the above natural herbs and plants have been individually utilized in traditional Chinese folk medicines for a variety of treatments, it has not been previously disclosed that the active components described above in combination would produce a composition with the remarkable synergistic therapeutic effects of the compositions of the present invention.

The present invention is predicated primarily on the unexpected discovery that the aqueous extracts of the above-listed Chinese plants and herbs combine to produce a new, highly effective, non-toxic therapeutic agent for the treatment of cardiovascular disease, cerebrovascular disease, SDAT and depression occurring either singly or in combination with each other. These aqueous extracts are comprised of novel biologically active components apparently produced by reactions between the compounds present in the Chinese plants and herbs that are significantly different in chemical nature from the starting materials. The resulting new chemical compositions dictate a change in the pharmaceutical properties of the aqueous extracts. Accordingly, it is critical to the success of the invention that aqueous extracts or derivatives of each of the listed Chinese plants be included in the pharmaceutical composition.

The medicines exhibit the highly advantageous combination of being relatively inexpensive, highly effective and of low toxicity.

The compositions of the invention are remarkably effective against cardiomyopathy, myocardial infarction, cerebral infarction, arrhythmia, cardiovascular disease, myocarditis and cerebrovascular disorders. They also show a positive response in patients with mild and moderate forms of brain disorders such as Alzheimer's disease. They are useful as an anti-depressant for treating severe depression. Furthermore, they exhibit no detectable hazardous side effects.

Figure 1:
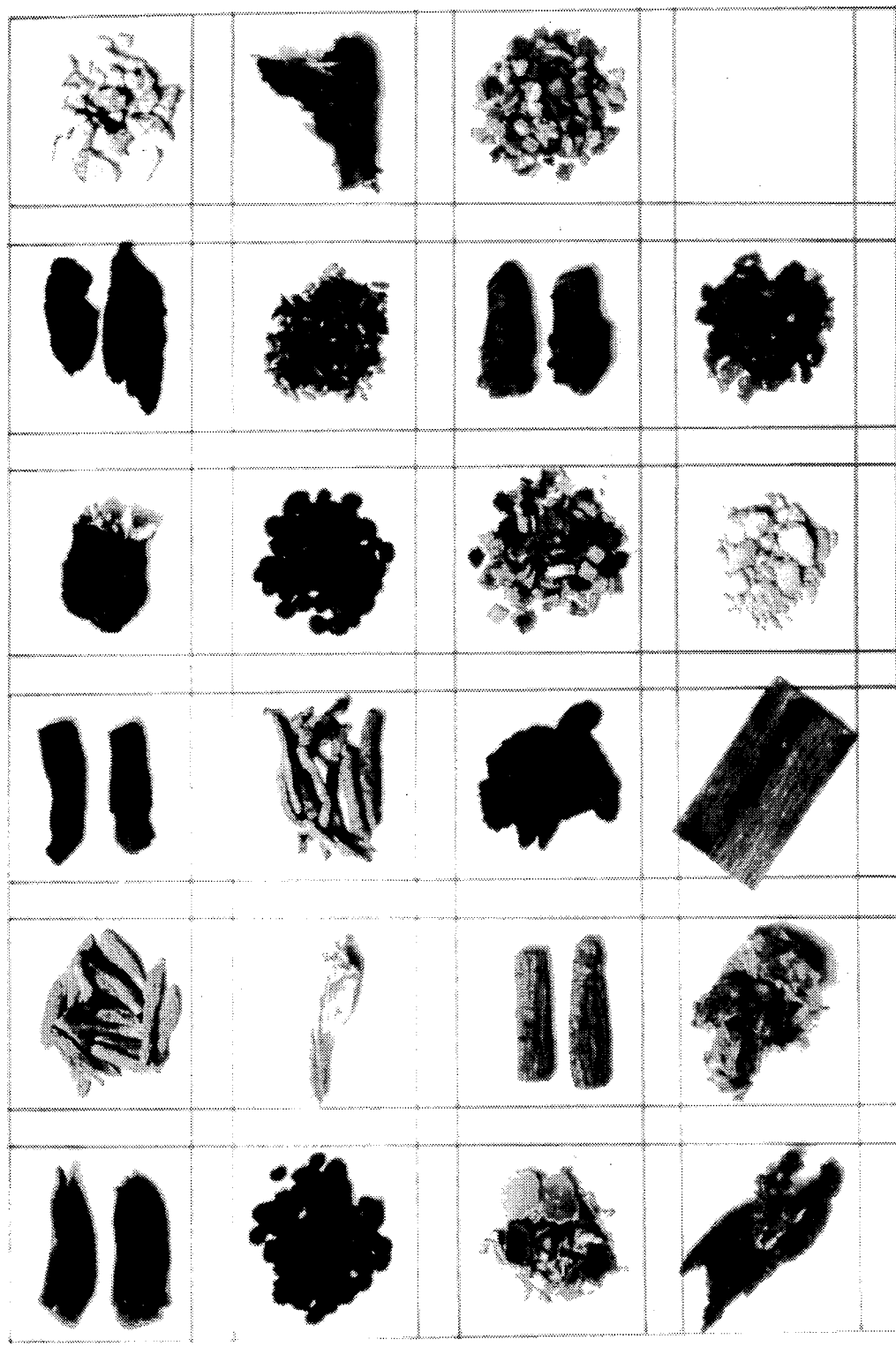
FIG. 1 shows photographs of the starting Chinese plants used to produce the medicines of the present invention, the identity of which (from top left to right) is as follows: (1) *Asparagus cochinchinensis,* (2) *Ophiopogon japonicus,* (3) *Salvia miltiorrhiza,* (4) *Angelica aeutiloba kitagawa,* (5) *Rehmannia glutinosa Liboschitz,* (6) *Poria cocos wolf,* (7) *Schizandra chinensis,* (8) *Platycodon grandiflorum,* (9) *Polygala tenuifolia,* (10) *Zizyphus jujuba,* (11) *Biota orientalis,* (12) *Pueraria pseudo-hirsuta,* (13) *Panax ginseng,* (14) *Codonopsis pilosula,* (15) *Scrophularia ningpoensis,* (16) *Glycyrrhiza uralensis,* (17) *Panax pseudo-ginseng,* (18) *Ganoderma japonicum,* (19) *Coptis chinensis,* (20) *Chrysanthemum morifolium,* (21) *Phellodendron amurense,* (22) *Red ginseng* and (23) Amber.

The compositions of this invention are derived from various combinations of the following Chinese plants and herbs: (1) *Asparagus cochinchinensis*, (2) *Ophiopogon japonicus*, (3) *Salvia miltiorrhiza*, (4) *Angelica aeutiloba kitagawa*, (5) *Rehmannia glutinosa Liboschitz*, (6) *Poria cocos wolf*, (7) *Schizandra chinensis*, (8) *Platycodon grandiflorum*, (9) *Polygala tenuifolia*, (10) *Zizyphus jujuba*, (11) *Biota orientalis*, (12) *Pueraria pseudo-hirsuta*, (13) *Panax ginseng*, (14) *Codonopsis pilosula*, (15) *Scrophularia ningpoensis*, (16) *Glycyrrhiza uralensis*, (17) *Panax pseudo-ginseng*, (18) *Ganoderma japonicum*, (19) *Coptis chinensis*, (20) *Chrysanthemum morifolium*, (21) *Phellodendron amurense*, (22) *Red ginseng* and (23) *Amber*. These starting materials are also set forth in Table 1 with the preferred amounts of each listed for preparing the compositions of the invention. Their photographs are shown in FIG. 1. In addition, each is described in detail with regard to its origin, physical properties and chemical composition in Example 1. As previously mentioned, all of the raw materials are readily obtainable from several commercial sources in China, Taiwan, Japan and other Southeast Asian countries.

The medicine of this invention has been formulated into four compositions in order to vary the potency for patients in different stages of the illnesses noted above. These compositions have been designated TP 93-U, TP 93-G, TP 93-PI and TP 93-PII wherein U, G and P denote urgent, general and preventive, respectively. TP 93-U is the strongest, most effective formula and, thus, is suitable for acute symptoms. TP 93-G has moderate potency particularly adapted for use on symptoms of a general nature. TP 93-PI and TP 93-PII are two mild versions especially suitable for long-term care and preventive purposes. As will be explained hereinbelow, the difference between TP 93-PI and TP 93-PII is that the raw materials of the former must first be boiled in water so as to obtain an aqueous solution which is orally administrable to patients, whereas the latter does not require prior cooking and is prepared by grinding the raw materials into a fine powder which is orally administrable to patients.

The amounts of each plant material to be utilized in preparing the extract of the invention may be varied as follows (Table 1):

TABLE 1

COMPOSITIONS FOR MEDICINES TP 93-U, TP 93-G, TP 93-PI AND TP 93-PII

| No. | Chinese Plant | Wt. % Ranges Based on Total Wt. of Plant Material | | | |
|---|---|---|---|---|---|
| | | TP 93-U | TP 93-G | TP 93-PI | TP 93-PII |
| (1) | *Asparagus cochinchinensis* | 5 to 20 | 3 to 15 | 5 to 20 | — |
| (2) | *Ophiopogon japonicus* | 5 to 20 | 3 to 15 | 2 to 10 | — |
| (3) | *Salvia miltiorrhiza* | 5 to 20 | 5 to 20 | 2 to 10 | 20 to 60 |
| (4) | *Angelica aeutiloba* kitagawa | 5 to 20 | 3 to 15 | 2 to 10 | — |
| (5) | *Rehmannia glutinosa* Liboschitz | 5 to 20 | 5 to 20 | 2 to 10 | — |
| (6) | *Poria cocos* wolf | 5 to 16 | 5 to 20 | 2 to 10 | — |
| (7) | *Schizandra chinensis* | 1 to 15 | 2 to 15 | 2 to 10 | — |
| (8) | *Platycodon grandiflorum* | 1 to 6 | 1 to 5 | 2 to 4 | — |
| (9) | *Polygala tenuifolia* | 1 to 10 | 2 to 15 | 2 to 10 | — |
| (10) | *Zizyphus jujuba* | 1 to 10 | 2 to 15 | 2 to 10 | — |
| (11) | *Biota orientalis* | 1 to 10 | 2 to 5 | 1 to 5 | — |
| (12) | *Pueraria pseudo-hirsuta* | 1 to 10 | 2 to 15 | 2 to 10 | — |
| (13) | *Panax ginseng* | 1 to 10 | 1 to 10 | 2 to 8 | — |
| (14) | *Codonopsis pilosula* | 1 to 20 | 2 to 15 | — | — |
| (15) | *Scrophularia ningpoensis* | 1 to 15 | 3 to 15 | 2 to 15 | — |
| (16) | *Glycyrrhiza uralensis* | 0.1 to 2 | 0.1 to 2 | 0.1 to 2 | — |
| (17) | *Panax pseudo-ginseng* | 1 to 15 | 3 to 15 | — | 20 to 60 |
| (18) | *Ganoderma japonicum* | 1 to 10 | 3 to 15 | 2 to 10 | — |
| (19) | *Coptis chinensis* | 1 to 5 | — | 1 to 5 | — |
| (20) | *Chrysanthemum morifolium* | 1 to 10 | — | 1 to 5 | — |
| (21) | *Phellodendron amurense* | 1 to 10 | — | — | — |
| (22) | Red ginseng | — | — | — | 10 to 30 |
| (23) | Amber | — | — | — | 5 to 20 |

The individual Chinese plant blends and the preferred amounts of each for use as starting materials for preparing compositions I, II, III and IV of the invention are as follows:

TP 93-U is extracted from a blend comprising the following 21 components: (1) *Asparagus cochinchinensis* (10 g), (2) *Ophiopogon japonicus* (8 g), (3) *Salvia miltiorrhiza* (8 g), (4) *Angelica aeutiloba kitagawa* (8 g), (5) *Rehmannia glutinosa Liboschitz* (10 g), (6) *Poria cocos wolf* (8 g), (7) *Schizandra chinensis* (5 g), (8) *Platycodon grandiflorum* (1.7 g), (9) *Polygala tenuifolia* (3 g), (10) *Zizyphus jujuba* (3 g), (11) *Biota orientalis* (3 g), (12) *Pueraria pseudo-hirsuta* (3 g), (13) *Panax ginseng* (2 g), (14) *Codonopsis pilosula* (5 g), (15) *Scrophularia ningpoensis* (4 g), (16) *Glycyrrhiza uralensis* (0.5 g), (17) *Panax pseudo-ginseng* (5 g), (18) *Ganoderma japonicum* (3 g), (19) *Coptis chinensis* (2 g), (20) *Chrysanthemum morifolium* (5 g) and (21) *Phellodendron amurense* (3 g).

TP 93-G is prepared from a mixture of 18 components: (1) *Asparagus cochinchinensis* (3 g), (2) *Ophiopogon japonicus* (4 g), (3) *Salvia miltiorrhiza* (5 g), (4) *Angelica aeutiloba kitagawa* (3 g), (5) *Rehmannia glutinosa Liboschitz* (5 g), (6) *Poria cocos wolf* (5 g), (7) *Schizandra chinensis* (3 g), (8) *Platycodon grandiflorum* (1.7 g), (9) *Polygala tenuifolia* (3 g), (10) *Zizyphus jujuba* (3 g), (11) *Biota orientalis* (3 g), (12) *Pueraria pseudohirsuta* (3 g), (13) *Panax ginseng* (1.5 g), (14) *Codonopsis pilosula* (3 g), (15) *Scrophularia ningpoensis* (4 g), (16) *Glycyrrhiza uralensis* (0.5 g), (17) *Panax pseudo-ginseng* (3 g) and (18) *Ganoderma japonicum* (3 g).

TP 93-PI is derived from the following 18 components: (1) *Asparagus cochinchinensis* (10 g), (2) *Ophiopogon*

*japonicus* (4 g), (3) *Salvia miltiorrhiza* (3 g), (4) *Angelica aeutiloba kitagawa* (3 g), (5) *Rehmannia glutinosa Liboschitz* (3 g), (6) *Poria cocos wolf* (3 g), (7) *Schizandra chinensis* (3 g), (8) *Platycodon grandiflorum* (1 g), (9) *Polygala tenuifolia* (3 g), (10) *Zizyphus jujuba* (3 g), (11) *Biota orientalis* (2 g), (12) *Pueraria pseudo-hirsuta* (3 g), (13) *Panax ginseng* (2 g), (14) *Scrophularia ningpoensis* (3 g), (15) *Glycyrrhiza uralensis* (0.5 g), (16) *Ganoderma japonicum* (2 g), (17) *Coptis chinensis* (1 g) and (18) *Chrysanthemum morifolium* (2 g).

Unlike the previous three formulations, TP 93-PII has a simple composition comprising only four components: (1) *Salvia miltiorrhiza* (3 g), (2) *Panax pseudo-ginseng* (2 g), (3) *Red ginseng* (1 g) and (4) *Amber* (0.5 g).

The above-listed preferred compositions are also summarized in Table 2.

TABLE 2

PREFERRED COMPOSITIONS FOR MEDICINES TP 93-U, TP 93-G, TP 93-PI AND TP 93-PII

| No. | Starting Material | TP 93-U | TP 93-G | TP 93-PI | TP 93-PII |
|---|---|---|---|---|---|
| 1 | *Asparagus cochinchinensis* | 10 | 3 | 10 | — |
| 2 | *Ophiopogon japonicus* | 8 | 4 | 4 | — |
| 3 | *Salvia miltiorrhiza* | 8 | 5 | 3 | 3 |
| 4 | *Angelica aeutiloba* kitagawa | 8 | 3 | 3 | — |
| 5 | *Rehmannia glutinosa* Liboschitz | 10 | 5 | 3 | — |
| 6 | *Poria cocos* wolf | 8 | 5 | 3 | — |
| 7 | *Schizandra chinensis* | 5 | 3 | 3 | — |
| 8 | *Platycodon grandiflorum* | 1.7 | 1.7 | 1 | — |
| 9 | *Polygala tenuifolia* | 3 | 3 | 3 | — |
| 10 | *Zizyphus jujuba* | 3 | 3 | 3 | — |
| 11 | *Biota orientalis* | 3 | 3 | 2 | — |
| 12 | Pueraria pseudo-hirsuta | 3 | 3 | 3 | — |
| 13 | Panax ginseng | 2 | 1.5 | 2 | — |
| 14 | *Codonopsis pilosula* | 5 | 3 | — | — |
| 15 | *Scrophularia ningpoensis* | 4 | 4 | 3 | — |
| 16 | *Glycyrrhiza uralensis* | 0.5 | 0.5 | 0.5 | — |
| 17 | Panax pseudo-ginseng | 5 | 3 | — | 2 |
| 18 | *Ganoderma japonicum* | 3 | 3 | 2 | — |
| 19 | *Coptis chinensis* | 2 | — | 1 | — |
| 20 | *Chrysanthemum morifolium* | 5 | — | 2 | — |
| 21 | *Phellodendron amurense* | 3 | — | — | — |
| 22 | Red ginseng | — | — | — | 1 |
| 23 | Amber | — | — | — | 0.5 |
| | TOTAL WEIGHT, g | 100.2 | 56.7 | 51.5 | 6.5 |

It is preferable to prepare the compositions for TP 93-U, TP 93-G and TP 93-PI by mincing the mixture of the starting materials and placing it in a container. Water in an amount 10 to 20 times by weight of the mixture is added and the contents are brought to a boil. During boiling, water is allowed to escape to reduce its volume. The water should be reduced to one-half or one-third of its original volume. Boiling time may vary from 30 minutes to 4 hours, but ideally should be between 1–2 hours. Since boiling beyond 2 hours does not change the chemical compositions of the three medicines, it is not harmful to extend the boiling time beyond 2 hours. However, it is not desirable to boil the mixture for less than 1 hour because complete extraction of the medicine may not occur. After boiling for 1 to 2 hours, the solid residue is removed by, e.g., simple filtration. The residue is considered to be waste and is thus discarded. The dark brown filtrate obtained can be orally administered to patients. The filtrate may be divided into two or three equal portions for administration two or three times daily.

TP 93-PII is preferably prepared by grinding the mixture of the four components and the resulting fine powder is administered orally. Because its preparation does not require a prior cooking as does the preparation of the other three medicines, TP 93-PII is more convenient than TP 93-PI. However, both TP 93-PII and TP 93-PI have similar therapeutic effectiveness on cardiovascular disease, cerebrovascular disease, SDAT and depression.

In addition to solution form, TP 93-U, TP 93-G and TP 93-PI can also be made into other forms. The solution can be concentrated and dried. The dried powder obtained may be pressed into granules, pellets and powder and formulated into tablets or capsules employing conventional pharmacological techniques.

All of the medicines of this invention can be readily made into a delicious health drink. The dried powder or concentrated aqueous solution may be mixed with a syrup formula and then carbonated water added thereto. The amount of the medicine powder may be varied from 2 to 50% by weight of the total composition, and preferably is 5–15%.

Furthermore, all of the medicines of the invention may be parenterally administered, e.g., injected into the human blood system, for they are very soluble in water. However, further isolation and purification of the major active components by a chromatographic technique may be required for administration by injection. The compositions may also be administered by an infusion technique.

The diseases for which the medicines of this invention are particularly effective include cardiomyopathy, myocardial infarction, cerebral infarction, arrhythmia, cardiovascular disease, myocarditis and cerebrovascular disorder. The medicines are also effective in treating brain disorders such as Alzheimer's disease, particularly in the early stages thereof. In addition, the medicines are useful as anti-depressant drugs.

The dosage administered to a particular patient will depend upon a variety of conditions, i.e., the disease(s) under treatment and the severity thereof, the age and condition of the patient, etc. Generally, however, a dosage of from about 20 to about 600 mg of extracted material (or ground tissue in the case of composition IV) per kg of body weight may be administered daily, preferably divided into three equal doses.

Despite a history of several thousand years in clinical applications, the mechanisms by which Chinese medicines function remains a mystery to the medical community at large.

During the last three decades, significant advances have been made in understanding the physical and chemical properties of individual Chinese medicines. However, essentially nothing is known about medicines extracted after combining individual Chinese medicines. It is reasonable to suggest that the first step towards understanding the pharmacology of a medicine derived from several Chinese medicines is to understand its chemistry. For this reason, the physical and chemical properties of TP 93-U, TP 93-G, TP 93-PI and TP 93-PII have been investigated. It is interesting to note that despite their obvious differences in component ratios and constituent components, they have surprisingly similar physical and chemical properties. For example, their pH values vary in a narrow range of 4.0 to 5.21. Furthermore, all have the same major component which ranges from 84 to 60 mol % of the total concentration.

There is sufficient evidence to suggest that this major component does not originate from one of the starting Chinese medicines used; rather, it is a reaction product formed in the process of extracting the medicine previously described. It is possible that this major component plays an important role in the pharmacological activities of the medicine of the invention. However, the presence of the other components appears to be necessary in order to counteract the toxic effects of the major component.

The mechanism by which the medicines of the present invention work is not presently known. It is theorized that the medicines of this invention work by their ability to remove toxic substances in cells. Removal of the toxic substances would stimulate the growth of cells and thereby the growth of tissues and organs. This theory is supported by the finding that the nerve cells grew longer and extended to a significant degree in rats provided with the medicine as compared to rats that were not exposed thereto.

The following examples illustrate preparation and use of the medicines of the invention. It is to be understood, however, that the examples are merely illustrative and intended to enable those skilled in the art to practice the invention in all of the embodiments flowing therefrom. These examples do not in any way limit the scope of the invention as defined in the appended claims.

EXAMPLES

Example 1

Starting Materials

All of the starting Chinese materials used in this invention are readily available from several commercial sources in China, Japan, Taiwan and other Asian countries. They are relatively inexpensive. FIG. 1 shows their photographs. Following are descriptions of each of the starting materials in terms of its origin, physical properties and chemical composition. The information was obtained from two references:

(1) Choug Sun Medical School, "Chemical Applications of Chinese Medicines," translated into Japanese by Shin Fu Chinese Medicines Research Institute, Medicine Publisher (1979); and (2) Product Bulletins, Tochimoto Pharmaceutical Company, Osaka, Japan.

1. *Asparagus cochinchinensis Merrill* (Liliaceae)

Origin: After removal of the skins, the roots of the plant were steamed and dried.

Physical Properties: Bittersweet taste, 17.0% weight loss after drying, and less than 3% chart yield.

Principal chemical composition: Asparagine, β-sitosterol and 5-methoxymethylfurfural.

Formula:

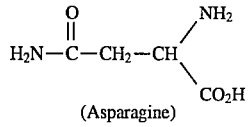
(Asparagine)

2. *Ophiopogon japonicus Ker-Gawler* (Liliaceae)

Origin: The dried thick portion of the plant roots.

Physical properties: Sweet with a slightly bitter taste.

Principal chemical composition: Glucose and starch mainly with small quantities of vitamin A and β-sitosterol.

Formula:

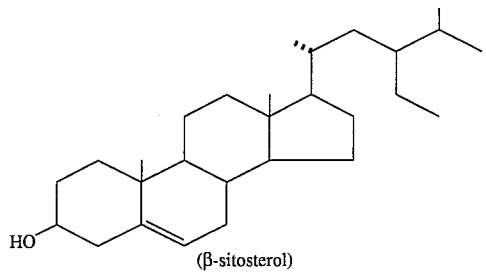
(β-sitosterol)

3. *Salvia miltiorrhiza Bge* (Labiatae)

Origin: Dried roots.

Physical properties: Bitter taste.

Principal chemical composition: Tanshinone A $C_{18}H_{12}O_3$, tanshinone B $C_{19}H_{18}O_3$ and tanshinone C $C_{19}H_{20}O_3$.

4. *Angelica aeutiloba kitagawa* (Umbelliferae)

Origin: Cooked and dried roots.

Physical properties: Leaves content less than 3%, more than 35% alcohol extractable material, chart yield less than 7%, and acid-insoluble material less than 1%.

Principal chemical composition: Ligustillide.

Formula:

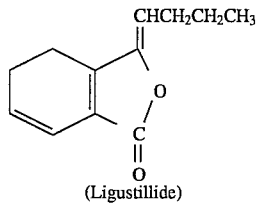
(Ligustillide)

5. *Rehmannia glutinosa Liboschitz* (Scrophulariaceae)

Origin: Steamed and dried roots.

Physical properties: Bittersweet taste, chart yield 6%, and 2.5% acid indigestible material.

Principal chemical composition: Rehmannin, xylitol, glucose, mannitol, iron, vitamin A and catalpol.

Formula:

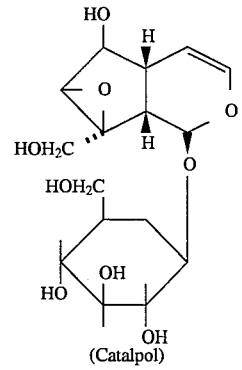
(Catalpol)

6. *Poria cocos wolf* (Polyporaceae)

Origin: The white stone-like material formed from bacteria grown on the surface of the underground root of a tree. The material was obtained by removing its outer skin.

Physical properties: Chart yield less than 1%.

Principal chemical composition: Ergosterol.

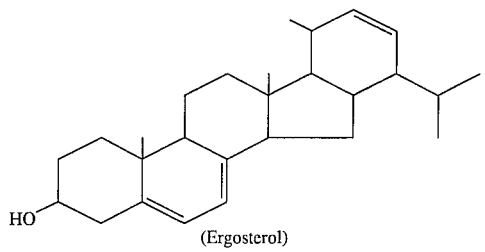
(Ergosterol)

7. *Schizandra Chinensis Baillon* (Schizandraceae)

Original: Ripe fruits dried.

Physical properties: Sour taste, chart yield less than 5%, and impurity less than 1%.

Principal chemical composition: Citral, schizandrin $C_{23}H_{32}O_6$, vitamins A and C and d-ylangene.

Formula:

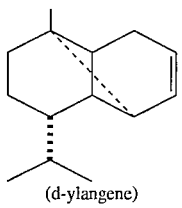
(d-ylangene)

8. *Platycodon grandiflorum A. De Candolle* (Campanulaceae)

Origin: Dried roots.

Physical properties: Bitter taste, chart yield less than 4%, and more than 25% alcohol extractable material.

Principal chemical composition: Polygalacic acid platycoside (hydrolysis leads to platycodigenin $C_{23}H_{38}O_5$), inulin and phytosterol.

Formula:

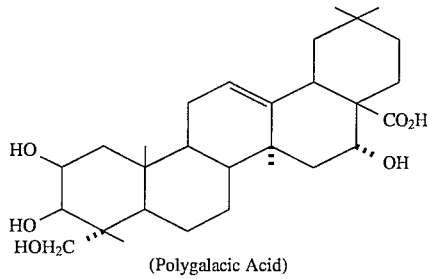
(Polygalacic Acid)

9. *Polygala tenuifolia Willd.* (Polygalaceae)

Origin: Roots dried after removing center portion.

Physical properties: Bitter taste.

Principal chemical composition: Tenuifolin (hydrolysis gives tenuigenin A $C_{27}H_{40}O_8$ and tenuigenin B $C_{30}H_{46}O_3$), polygallitol $C_6H_{12}O_5$ and onsicin $C_{24}H_{47}O_5$.

10. *Zizyphus jujuba Miller* (*Zizyphus Vulgaris lamarck* var. *spinosus Bunge*) (Rhamnaceae)

Origin: Dried seeds.

Physical properties: Bittersweet taste, seed inner skin less than 4% and chart yield less than 5%.

Principal chemical composition: Betulinic acid $C_{30}H_{48}O_3$, betulin $C_{30}H_{50}O_2$, β-sitosterol, fatty acids, vitamin A and organic acids.

Formula:

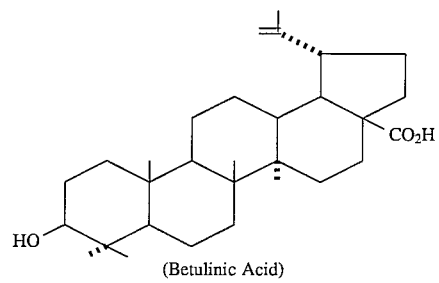
(Betulinic Acid)

11. *Biota orientalis endl.* (Cupressaceae)

Origin: Dried seeds.

Physical properties: Sweet taste.

Principal chemical composition: Borneol and fatty acids.

12. *Pueraria pseudo-hirsuta Tang at Wang* (Leguminosae)

Origin: Dried roots.

Physical properties: Sweet taste.

Principal chemical composition: Flavon, puerarin, daidzein and other kinds of flavon.

13. *Panax ginseng C.A. Mayer* (*Panax schinseng Nees*) (Araliaceae)

Origin: Roots boiled and dried after removing thin roots.

Physical properties: Sweet with slightly bitter taste, chart yield less than 4.2%, and 14% alcohol extractable material.

Principal chemical composition: Ginsenoside, panacene $C_{15}H_{24}$, panaquilon $C_{3256}O_{14}$, panaxin $C_{23}H_{38}O_{10}$, various organic acids, vitamins A, $B_1$, $B_2$ and C, inorganic salts and starch.

Formula:

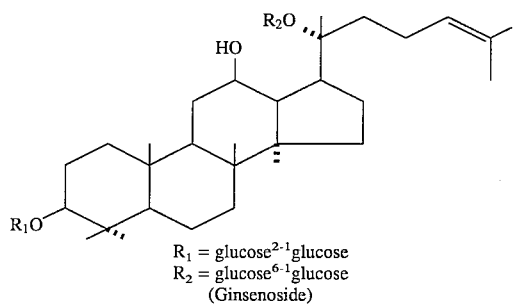
$R_1$ = glucose$^{2-1}$glucose
$R_2$ = glucose$^{6-1}$glucose
(Ginsenoside)

14. *Codonopsis pilosula* (Campanulaceae)

Origin: Dried roots.

Physical properties: Sweet taste.

Principal chemical composition: Alkaloid, saponin, protein, starch and vitamins $B_1$ and $B_2$.

15. *Scrophularia ningpoensis Hemsley* (Scrophulariaceae)

Origin: Dried roots of either *scrophularia ningpoensis Hemsley* or *Scyophularia buergeriana Miquel.*

Physical properties: Bitter/salty taste, chart yield less than 6%, acid-insoluble material less than 2%, and weight loss after drying 17%.

Principal chemical composition: Harpagide, phytosterol, linoleic acid and alkaloid.

Formula:

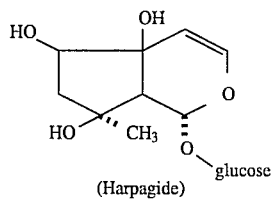

(Harpagide)

16. *Glycyrrhiza uralensis Fisch.* (Leguminosae)

Origin: Dried roots.

Physical properties: Sweet taste.

Principal chemical composition: Glycyrrhizic acid, calcium and potassium salts, glycyrrhizin (sweetening agent), glycyrrhizic acid upon hydrolysis gives glucuronic acid and glycyrrhetic acid, liquiritigenin $C_{21}H_{22}O_9$, glucose, mannitol, malic acid and l-asparagine.

17. *Panax pseudo-ginseng wall.* (Araliaceae)

Origin: Roots dried after removing skin.

Physical properties: Sweet with slightly bitter taste.

Principal chemical composition: Pseudo-ginseng A $C_{30}H_{52}O_{10}$, pseudo-ginseng B $C_{23}H_{38}O_{10}$ and flavon.

18. *Ganoderma japonicum Lloyd* (Polyporaceae)

Origin: Whole plant dried.

Physical properties: Sweet taste.

Principal chemical composition: Amino acid, protein, sterol and alkaloid.

19. *Coptis Chinensis Franch.* (Ranunculaceae)

Origin: Dried roots.

Physical properties: Bitter taste.

Principal chemical composition: Berberine $C_{20}H_{19}O_5N$, coptisine $C_{19}H_{15}O_5N$, palmatine $C_{21}H_{23}O_5N$ and woorenine $C_{20}H_{17}O_5N$.

20. *Chrysanthemum morifolium Ramat* (Compositae)

Origin: Dried flower heads.

Physical properties: Bittersweet taste.

Principal chemical composition: Adenine $C_5H_5N_5$, stachydrine $C_7H_{13}NO$, choline and oil.

21. *Phellodendron amurense Rupr.* (Rutaceae)

Origin: Dried skins of a yellow tree.

Physical properties: Bitter taste.

Principal chemical composition: Berberine, obakunone $C_{26}H_{30}O_7$, obakulactone $C_{26}H_{30}O_8$ and dictammolactone $C_{28}H_{30}O_9$.

22. *Red ginseng* (Araliaceae)

Origin: Dried ginseng roots.

Physical properties: Sweet with slightly bitter taste, chart yield less than 4.2%, and 14% alcohol extractable material.

Principal chemical composition: Ginsenoside, panacene $C_{15}H_{24}$, panaquilon $C_{32}H_{56}O_{14}$, panaxin $C_{23}H_{38}O_{10}$, various organic acids, vitamins A, $B_1$, $B_2$ and C, inorganic salts and starch.

23. Amber

Origin: A hard yellowish to brownish translucent fossil resin buried between the roots of an old tree.

Physical properties: Sweet taste.

Principal chemical composition: Succinoabietinolic acid $C_{40}H_{60}O_5$, succinogiluinic acid $C_{24}C_{36}O_2$, succinoresinol, succinoabietinol $C_{40}H_{60}O$ and fatty acids.

Example 2

TP 93-U Preparation and Characterization

The formula designated TP 93-U is the strongest and most effective medicine of the present invention. It is intended for use in patients in acute stages of cardiovascular disease, cerebrovascular disease, Alzheimer's disease and depression. Its preparation and usage are illustrated below.

As listed in Table 2, the following 21 Chinese plants were combined: (1) *Asparagus cochinchinensis* (10 g), (2) *Ophiopogon japonicus* (8 g), (3) *Salvia miltiorrhiza* (8 g), (4) *Angelica aeutiloba kitagawa* (8 g), (5) *Rehmannia glutinosa Liboschitz* (10 g), (6) *Poria Cocos wolf* (8 g), (7) *Schizandra chinensis* (5 g), (8) *Platycodon grandiflorum* (1.7 g), (9) *Polygala tenuifolia* (3 g), (10) *Zizyphus jujuba* (3 g), (11) *Biota orientalis* (3 g), (12) *Pueraria pseudo-hirsuta* (3 g), (13) *Panax ginseng* (2 g), (14) *Codonopsis pilosula* (5 g), (15) *Scrophularia ningpoensis* (4 g), (16) *Glycyrrhiza uralensis* (0.5 g), (17) *Panax pseudo-ginseng* (5 g), (18) *Ganoderma japonicum* (3 g), (19) *Coptis chinensis* (2 g), (20) *Chrysanthemum morifolium* (5 g) and (21) *Phellodendron amurense* (3 g). The mixture was placed in a container and 1,000 ml of water was added. The contents were heated to boil for 2 hours. During boiling, the water was allowed to evaporate in order to reduce the liquid volume. While warm, the solid residue was filtered to yield approximately 400 ml of dark brown liquid medicine. This medicine was divided into three equal portions to be orally administered three times daily. The medicine has a sweet and slightly sour, but not bitter, taste.

To determine the physical composition of the medicine, the solid residue was dried in an oven at 100° C. overnight, yielding 57.2 g of dark brown solid waste. The liquid medicine was concentrated using a rotary evaporator, followed by drying in an oven at 100° C. for 4 hours to produce 16.9 g of dried powder. The weight loss, attributable to water and volatile contents of the mixture comprising the above-mentioned 21 Chinese medicines was calculated to be 25.9%. Table 2 summarizes the physical compositions.

In order to gain a basic understanding of TP 93-U, the physical and chemical properties of the medicine powder obtained above were investigated and the results were as follows: Table 3 shows the solubility of the medicine. Although alcohols are frequently used to extract Chinese medicines, this medicine was found to be insoluble in ethanol, but only slightly soluble in methanol. Thus, alcohols are not an effective solvent for extracting this medicine. In contrast, this medicine is very soluble in water. Thus, it can readily be absorbed into the body through the blood medium, administered by an injection method. This can be accomplished by obtaining a pure or nearly pure form of the principal component by liquid or gas chromatography. Table 4 gives the pH value of 4.0 in water at 22° C., which explains the sweet and slightly sour taste of the medicine. Gas chromatograms were obtained on a Schimadzu GC-7A gas chromatograph (GC) using a flame ionization detector and a PEG 20M column. The column temperature was increased from 100° C. to 250° C. at 8° C./min., and then held for 16 min. at a final temperature of 250° C. The injection port temperature was 250° C. Four GC analyses were made for each sample.

Figure 2A:
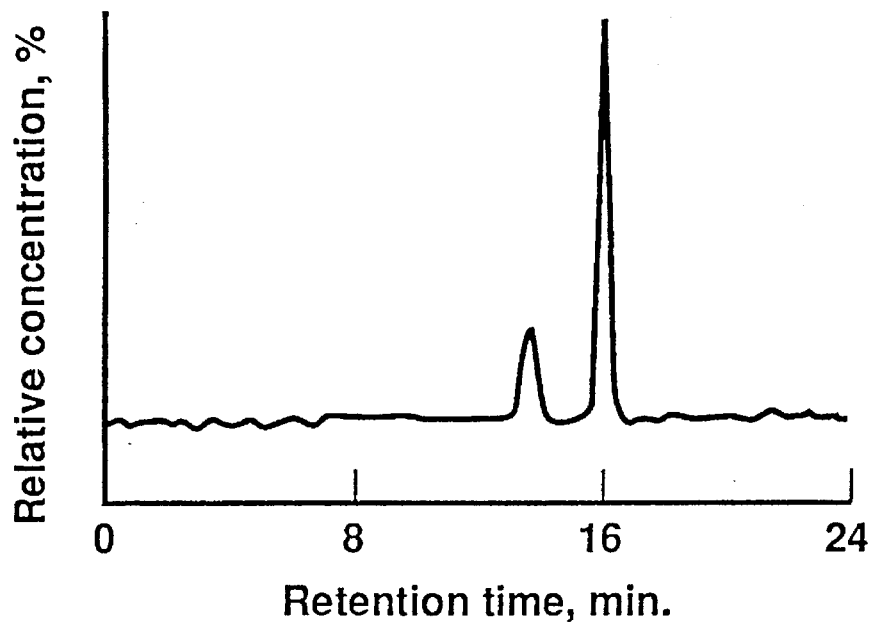
FIGS. 2a–2d show gas chromatograms of TP 93-U, TP 93-G, TP 93-PI and TP 93-PII (corresponding to compositions I, II, III and IV listed above), respectively.
Figure 2B:
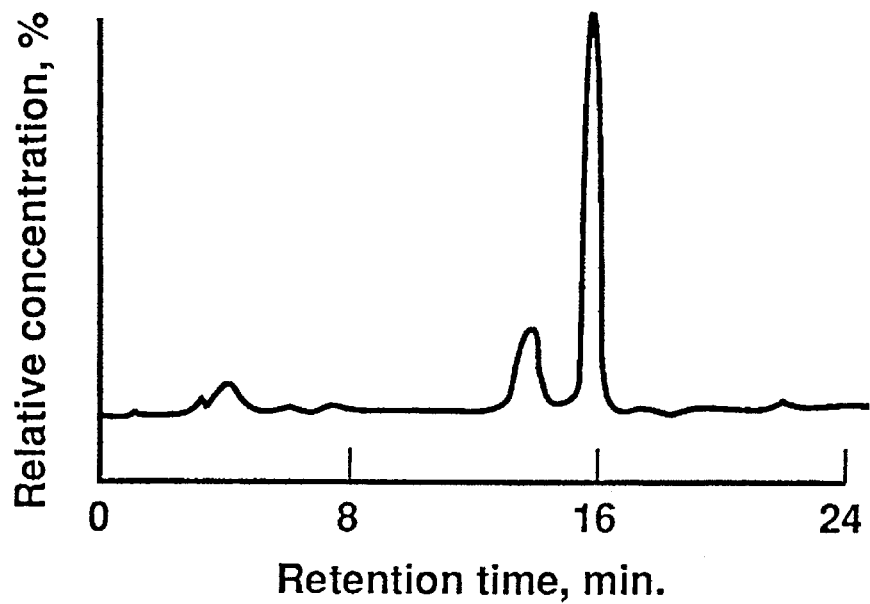
Figure 2C:
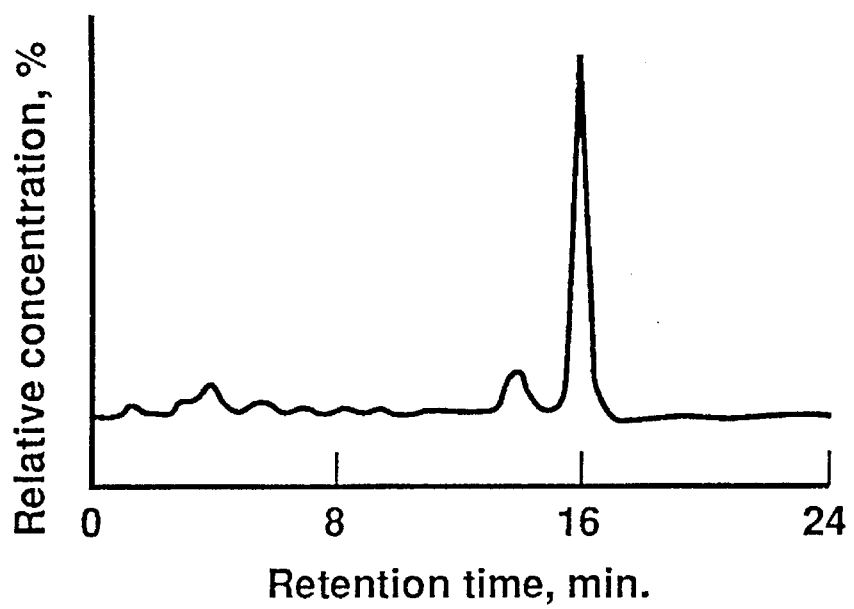
Figure 2D:
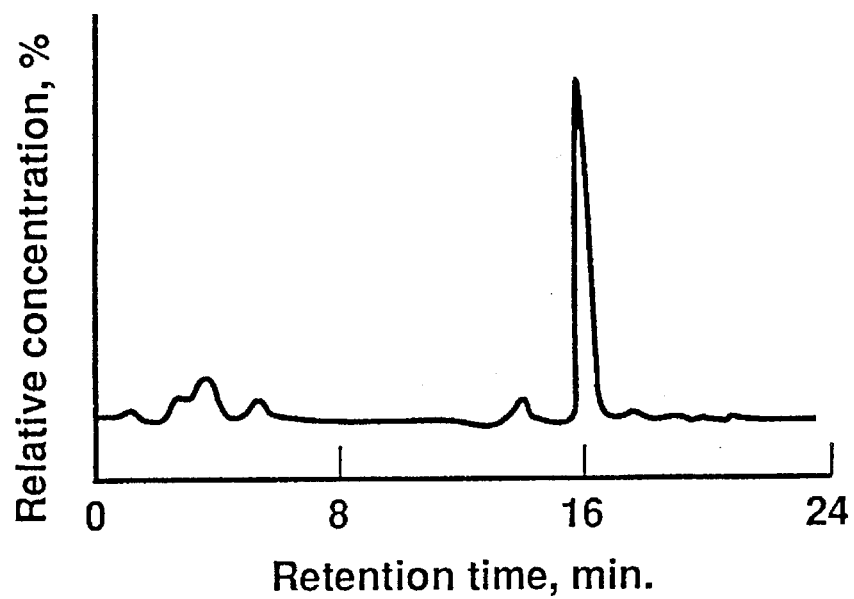

The reproducibility was excellent when a concentrated medicine aqueous solution was employed. FIG. 2a illustrates a typical chromatogram and Table 5 lists the chemical composition of TP 93-U, along with the other formulae.

There are 22 peaks seen in the chromatogram (FIG. 2a), corresponding to the 22 chemical components in this medicine. Among them, component No. 19 which has a 15.9 min. retention time was by far the major component, comprising 84.2 mol %. With the exception of component No. 17 which had a 12.9 min. retention time with 8.1% concentration, all of the remaining components had 1.0 or fractional percent concentration.

Figure 3:
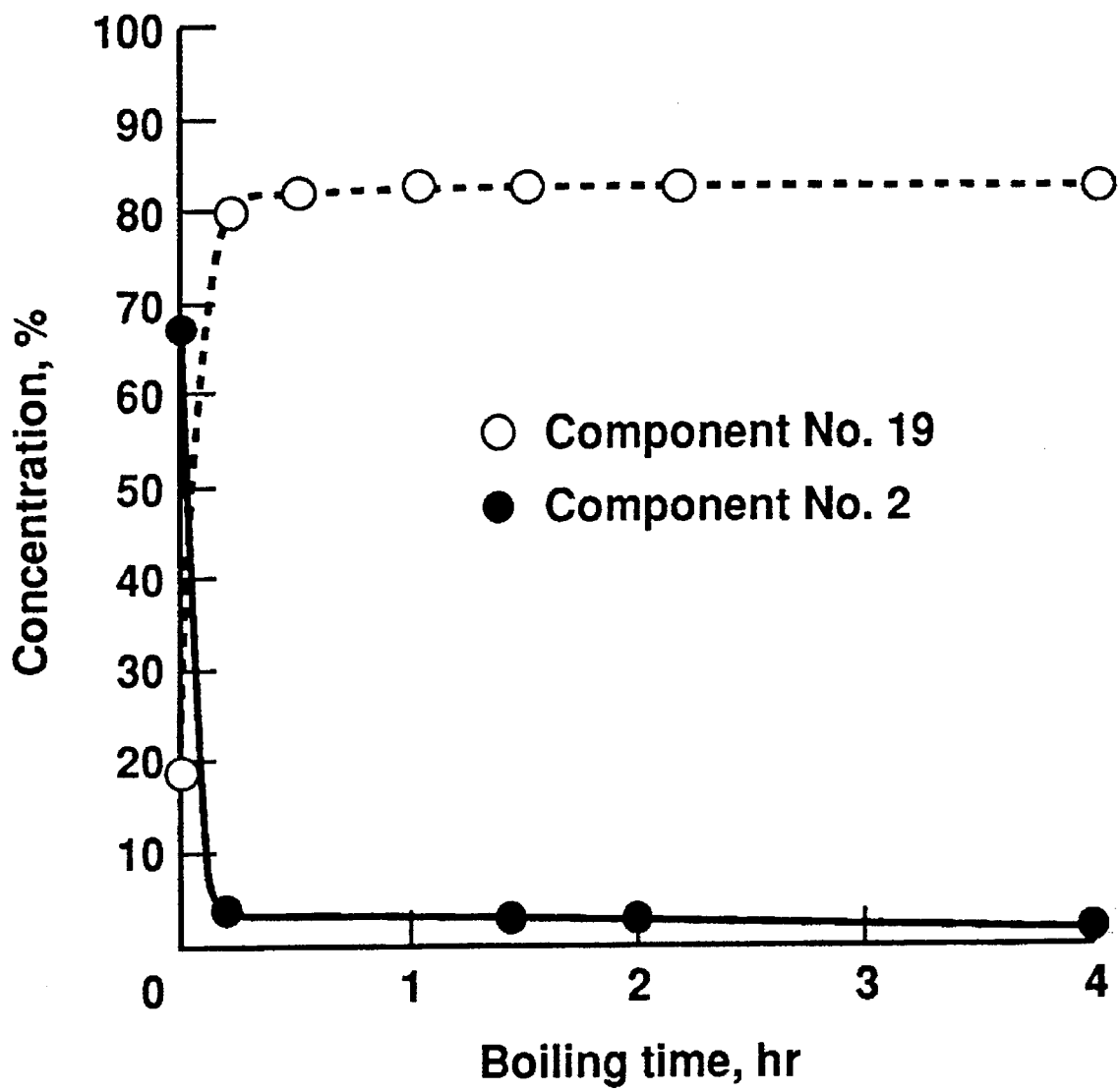
FIG. 3 is a plot of concentration as a function of boiling time, showing the increasing concentration of component 19 (major component), while the concentration of component 2 (presumably precursor of the major component) decreases, when the medicine boiling time increases.

To investigate the origin of this major component, a kinetics study was performed. A 10 ml sample was taken at each time interval of 0, 0.5, 1.0, 1.5, 2.0 and 4.0 hours during the boiling of the medicine mixture. The contents of these samples were analyzed by the GC technique noted above. As shown in FIG. 3, component No. 2 with 1.0 min. retention time had the highest concentration (68.2%) and component No. 19 with a 15.9 min. retention time had the second highest concentration (20.0%) at 0 hr. However, after 15 min. boiling time, the latter increased to 80.0%, whereas the former decreased to 2.3%. This finding suggests that the latter does not directly derive from the 21 starting materials, but rather is subsequently formed from the former as a precursor. It is theorized that the latter is a hydrolysis product of the former. Additional evidence arises from the pH value variation which decreased from 4.51 to 3.69 as the medicine boiling time increased from 0 to 4.0 hrs. These pH values are set forth in Table 6. The increased acidity and greater medicine concentration are factors responsible for the decrease in pH value.

Figure 4:
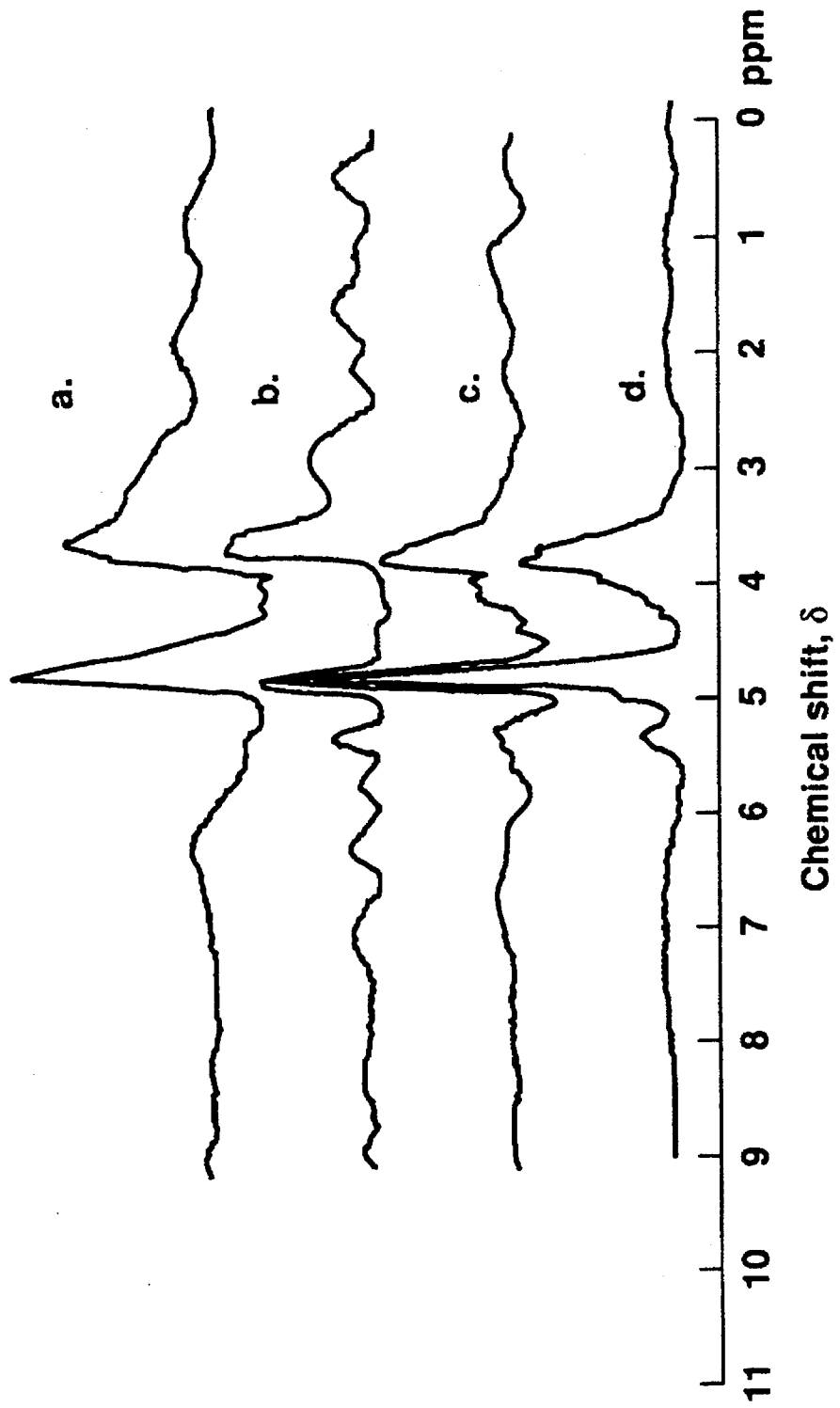
FIG. 4 shows $^1$H NMR spectra of TP 93-U (a), TP 93-G (b), TP 93-PI (c) and TP 93-PII (d).
Figure 5:
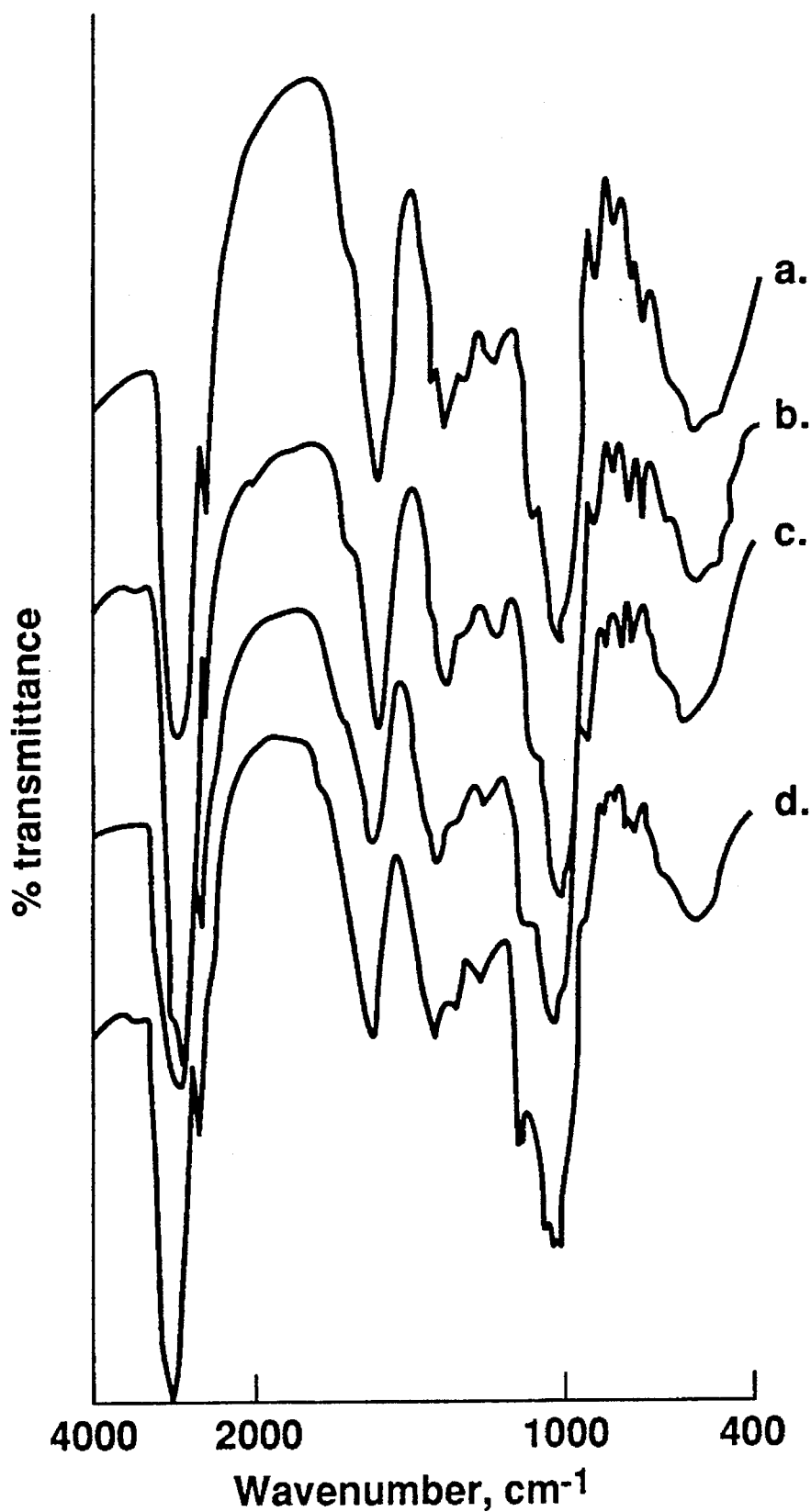
FIG. 5 shows FT-IR spectra of TP 93-U (a), TP 93-G (b), TP 93-PI (c) and TP 93-PII (d).
Figure 6:
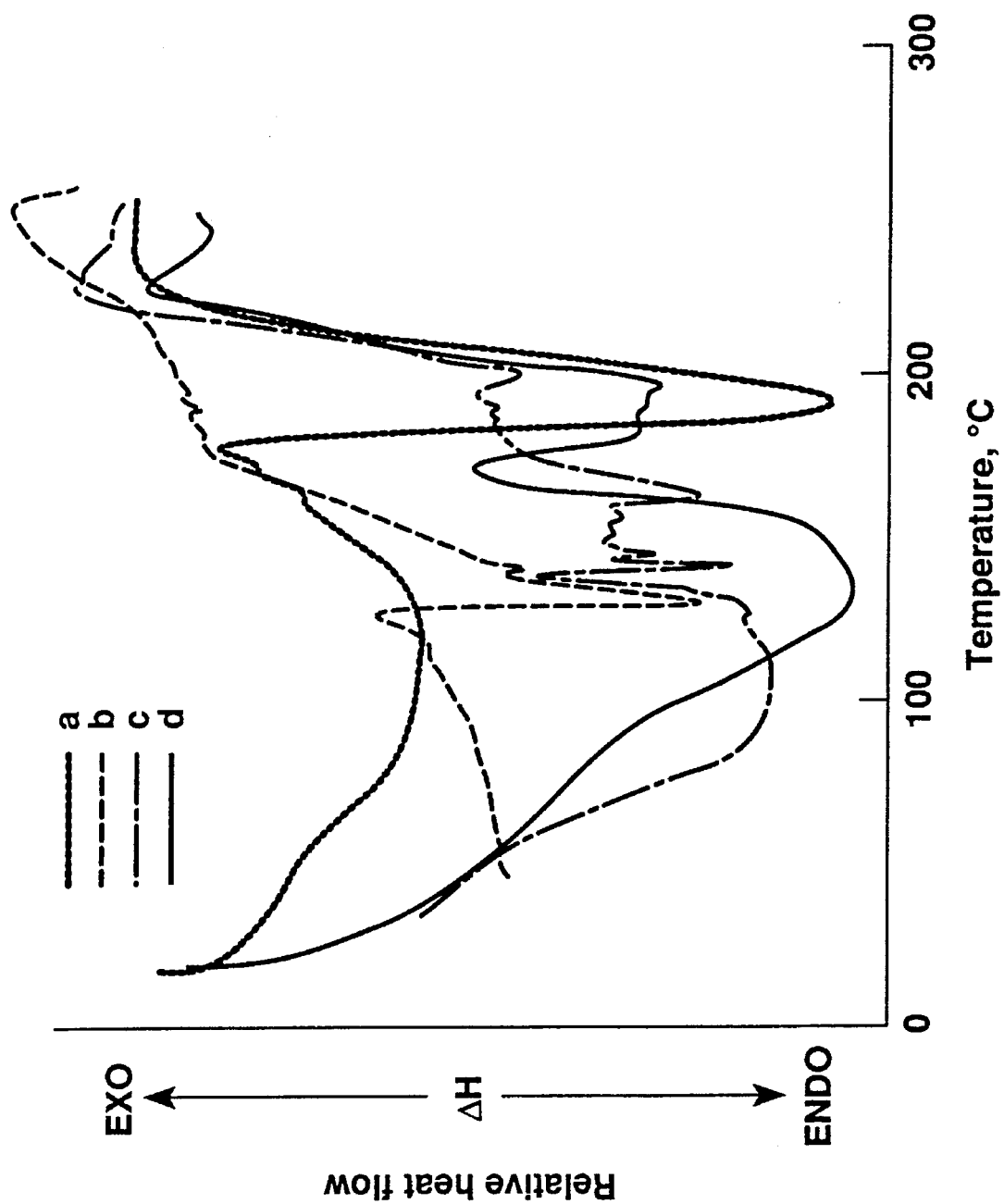
FIG. 6 shows differential scanning calorimetry (DSC) scans of TP 93-U (a), TP 93-G (b), TP 93-PI (c) and TP 93-PII (d).
Figure 7:
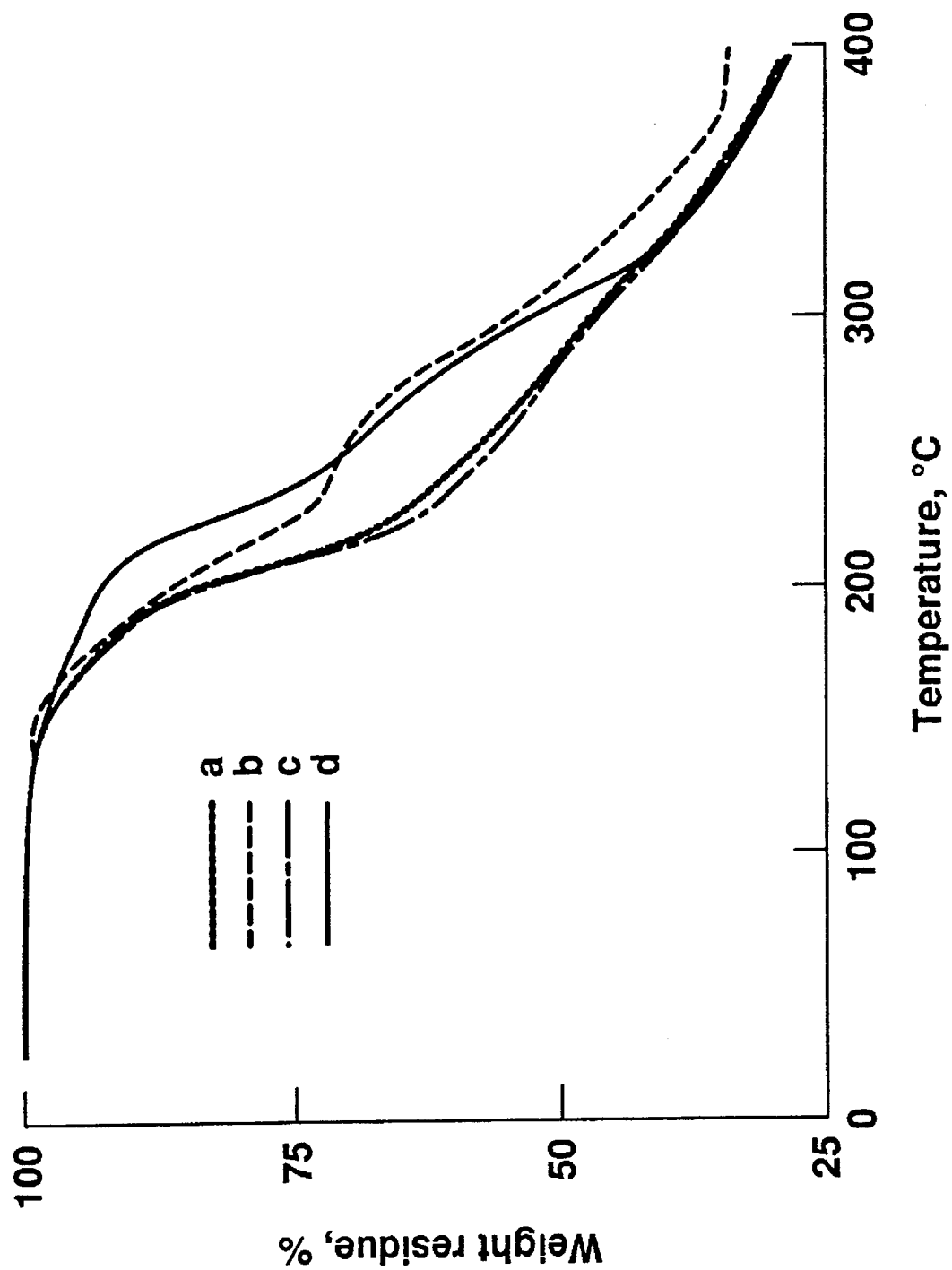
FIG. 7 shows thermogravimetric analysis (TGA) curves for TP 93-U (a), TP 93-G (b), TP 93-PI (c) and TP 93-PII (d).

$^1$H NMR spectra were recorded on a Jeol JNM-FX90Q spectrometer operating at 89.6 MHz and using $D_2O$ as a solvent. FIG. 4a shows the $^1$H NMR spectrum of medicine TP 93-U. The broad signal at δ4.75 is due to water. The broad $^1$H NMR peaks resulted from using a highly concentrated and viscous solution. FT-IR were measured in a KBr pellet on a Schimadzu FT-IR 8100 spectrophotometer. FIG. 5a shows the FT-IR spectrum. The strong absorption band around 3200 $cm^{-1}$ is attributed to water, conforming the results of the $^1$H NMR mentioned above. The differential scanning calorimetry (DSC) and thermogravimetric analysis (TGA) scans shown in FIGS. 6a and 7a, respectively, were performed using a Schimadzu DSC-41M thermal analyzer. The broad endotherm at 110° C. is due to water-induced softening of TP 93-U and the large sharp endothermic peak at 190° C. is undoubtedly due to the melting of the TP 93-U. The TGA data shown in FIG. 7a indicates that the medicine was stable up to 148° C. and, thereafter, rapid decomposition occurred.

Example 3

TP 93-G Preparation and Characterization

As in Example 2 above, a mixture consisting of the following 18 starting materials was prepared and added to 600 ml of water: (1) *Asparagus Cochinchinensis* (3 g), (2) *Ophiopogon japonicus* (4 g), (3) *Salvia miltiorrhiza* (5 g), (4) *Angelica aeutiloba kitagawa* (3 g), (5) *Rehmannia glutinosa Liboschitz* (5 g), (6) *Poria cocos wolf* (5 g), (7) *Schizandra chinensis* (3 g), (8) *Platycodon grandiflorum* (1.7 g), (9) *Polygala tenuifolia* (3 g), (10) *Zizyphus jujuba* (3 g), (11) *Biota orientalis* (3 g), (12) *Pueraria pseudo-hirsuta* (3 g), (13) *Panax ginseng* (1.5 g), (14) *Codonopsis pilosula* (3 g), (15) *Scrophularia ningpoensis* (4 g), (16) *Glycyrrhiza uralensis* (0.5 g), (17) *Panax pseudo-ginseng* (3 g) and (18) *Ganoderma japonicum* (3 g). The aqueous suspension was boiled for 2 hrs. After removal of the solid residue by filtration, approximately 200 ml of a dark brown medicine, TP 93-G, was obtained for daily oral administration.

This medicine was characterized in the same manner as in Example 1. Its physical and chemical properties are shown in the tables and figures, along with those of TP 93-U discussed in Example 1. Similarly to the principal component in TP 93-U, the major component in TP 93-G (component No. 19) was also a product of component No. 2 precursor based on the results of a kinetics study.

Example 4

TP 93-PI Preparation and Characterization

As in Example 1, the following 18 starting materials were combined, 600 ml of water was added thereto, the mixture was boiled for 2 hours and thereafter filtered to obtain 200 ml of a dark brown solution: (1) *Asparagus cochinchinensis* (10 g), (2) *Ophiopogon japonicus* (4 g), (3) *Salvia miltiorrhiza* (3 g), (4) *Angelica aeutiloba kitagawa* (3 g), (5) *Rehmannia glutinosa Liboschitz* (3 g), (6) *Poria cocos wolf* (3 g), (7) *Schizandra chinensis* (3 g), (8) *Platycodon grandiflorum* (1 g), (9) *Polygala tenuifolia* (3 g), (10) *Zizyphus jujuba* (3 g), (11) *Biota orientalis* (2 g), (12) *Pueraria pseudo-hirsuta* (3 g), (13) *Panax ginseng* (2 g), (14) *Scrophularia ningpoensis* (3 g), (15) *Glycyrrhiza uralensis* (0.5 g), (16) *Ganoderma japonicum* (2 g), (17) *Coptis Chinensis* (1 g) and (18) *Chrysanthemum morifolium* (2 g). The dark brown solution obtained was orally administrable to patients on a daily basis. Its properties are set forth in the tables and figures, along with those of TP 93-U and TP 93-G.

Example 5

TP 93-PII Preparation and Characterization

Unlike TP 93-U, TP 93-G and TP 93-PI which must be boiled in water and require a solution form for oral administration, TP 93-PII was prepared by simply grinding into fine powder a combination of the following four Chinese plants: (1) *Salvia miltiorrhiza* (3 g), (2) *Panax pseudoginseng* (2 g), (3) *Red ginseng* (1 g) and (4) Amber (0.5 g), followed by intimately admixing the powdered material to form a homogenous admixture. This powder, which has a pleasant taste, was orally administrable daily. The powder need not be extracted, but may be administered in powder form to the patient. The reactions referred to above with respect to aqueous extracts of the tissues between the compounds present in the tissues to produce a novel biologically active agent occurs in vivo when the powder is administered to the patient. For purposes of the chemical and physical characterization, the powder was boiled with water for 2 hrs. and was then analyzed following the same procedure as Example 2. Its physical and chemical properties are shown, along with those of the previous three medicines, in the tables and figures.

TABLE 3

Weight % of Medicine, Residue and Water/Volatiles

| Formula | Wt. % | | |
|---|---|---|---|
| | Medicine | Residue | Water/Volatile |
| TP 93-U | 16.9 | 57.2 | 25.9 |
| TP 93-G | 22.0 | 43.0 | 35.0 |
| TP 93-PI | 15.5 | 55.5 | 29.0 |
| TP 93-PII | 31.7 | 34.0 | 34.3 |

TABLE 4

Solubility

| Solvent | Formula | | | |
|---|---|---|---|---|
| | TP 93-U | TP 93-G | TP 93-PI | TP 93-PII |
| Water | +++ | +++ | +++ | +++ |
| Methanol | + | + | + | + |
| Ethanol | − | − | − | − |
| Methylene dichloride | − | − | − | − |
| Chloroform | + | + | + | + |
| Methylethylketone | − | − | − | − |
| N,N-dimethylacetamide | + | + | + | + |
| Dimethylformamide | + | + | + | + |
| Tetrahydrofuran | − | − | − | − |

+++ = very soluble; + = slightly soluble; − = insoluble.

TABLE 5 pH Values

| Formula | pH[1] |
|---|---|
| TP 93-U | 4.00 |
| TP 93-G | 4.05 |
| TP 93-PI | 4.11 |
| TP 93-PII | 5.21 |

[1]Measured in $H_2O$ at 22° C.

TABLE 6

Chemical Compositions

| Number | GC Retention Time, Min. | Concentration, %[1] | | | |
|---|---|---|---|---|---|
| | | TP 93-U | TP 93-G | TP 93-PI | TP 93-PII |
| 1 | 0.9 | 0.2 | — | 0.5 | 2.0 |
| 2 | 1.0 | 0.2 | 0.1 | 0.2 | 1.0 |
| 3 | 1.4 | 0.3 | 0.1 | — | — |
| 4 | 2.2 | 0.3 | 0.2 | 0.7 | 2.3 |
| 5 | 3.2 | 0.2 | 0.3 | — | — |
| 6 | 3.8 | 0.9 | — | — | — |
| 7 | 4.3 | 1.0 | 7.8 | 6.5 | 11.4 |
| 8 | 5.5 | 0.1 | 0.1 | — | — |
| 9 | 5.9 | 1.3 | 1.0 | 2.8 | 9.6 |
| 10 | 7.1 | 0.1 | — | — | — |
| 11 | 7.7 | 0.2 | 0.2 | — | — |
| 12 | 8.5 | 0.2 | 0.2 | 0.2 | — |
| 13 | 9.8 | 0.2 | 0.1 | — | — |
| 14 | 10.3 | 0.6 | 0.1 | 0.5 | — |
| 15 | 11.6 | 0.3 | 0.2 | 0.4 | 3.8 |
| 16 | 12.5 | 0.2 | 0.3 | 0.6 | 1.9 |
| 17 | 12.9 | 8.1 | 7.6 | 8.5 | 6.0 |
| 18 | 13.9 | 1.2 | 1.0 | 0.4 | 1.6 |
| 19 | 15.9 | 84.2 ± 1.1[2] | 80.8 ± 1.0[2] | 77.7 ± 2.0[2] | 60.2 ± 1.0[2] |
| 20 | 16.8 | 0.2 | 0.2 | 0.2 | 0.7 |
| 21 | 18.6 | 0.1 | — | 0.4 | — |
| 22 | 21.0 | 0.1 | — | 0.4 | — |

[1]average of 4 determinations;
[2]error

TABLE 7

Change in pH Value During Medicine Preparation

| Boiling Time (hr.) | pH[1] | |
|---|---|---|
| | TP 93-U | TP 93-G |
| 0.00 | 4.51 | 4.93 |
| 0.25 | 4.11 | 4.44 |
| 0.50 | 4.03 | 4.32 |
| 1.00 | 3.96 | 4.19 |
| 1.50 | 3.96 | 4.19 |
| 2.00 | 3.96 | 4.12 |
| 4.00 | 3.96 | 4.08 |

[1]Measured in $H_2O$ at 22° C.

The following examples illustrate the use of the medicine of the invention. To evaluate the results of the clinical tests, it is important to consider the following points: (1) The clinical tests were conducted primarily on the co-inventors, their relatives and friends. After failing to respond to the existing treatments, other patients were referred by the hospitals in Japan to the primary inventor, who is a fully licensed Japanese physician with 41 years of practical experience, including 15 years of clinical applications of Chinese medicines. (2) Among the 16 patients treated, 9 were males, 7 were females and their average age was 68 years. (3) During the period of the clinical tests, these patients were strictly forbidden to take other related drugs or treatments to prevent any counteracting of the effects of the medicines of this invention. (4) All of the patients are continuously taking the medicines of this invention in order to minimize recurrence of the symptoms or simply for care and prevention purposes. (5) To date, no detectable hazardous side effects due to the medicines of this invention have been observed.

Example 6

The co-inventor's father, age 78, has suffered from chronic heart disease for over 20 years. On Nov. 6, 1992, he experienced acute heart failure and was hospitalized in the intensive care unit. His attending physician's diagnosis indicated congestion of the lungs and liver due to the inadequate pumping action of his heart ventricle. Both of his legs and feet swelled to twice their normal size as a result of fluid accumulation in the surrounding tissues. He had severe problems with breathing, even when lying prone. After he was discharged from the hospital, he was still unable to walk and required assistance during his daily activities. He was then treated with TP 93-U. After 6 days, the accumulated fluid subsided considerably. He feels agile and has resumed his normal daily activities without any assistance.

Example 7

The primary inventor's wife, age 60, has also suffered from chronic heart disease for some time. Recently, she experienced the same symptoms described above in Example 6. Her feet and legs accumulated fluid and swelled, and she was unable to walk. After taking TP 93-G daily for 4 days, the symptoms disappeared.

Example 8

An 85-year-old male was hospitalized on Mar. 17, 1993. His attending doctor's prognosis was (1) multiple cerebral infarction, (2) anemia due to gastrointestinal bleeding, (3) chronic heart failure and (4) hypoheutrition. He has hemiparesis. Because of his advanced age, he was not recommended for surgical treatment. His doctor indicated that he probably had only 2–3 more days to live. The attending physician referred this patient to the primary inventor. After 8 days of daily treatment with TP 93-U, he made a remarkable recovery. Though still weak, he now has a good appetite and can carry out some light activities without assistance from others.

Example 9

The co-inventor has a family history of heart disease. She has had shortness of breath for more than 10 years. Since taking TP 93-PI starting on Dec. 15, 1992, she has not experienced such symptoms.

Example 10

The primary inventor had a severe case of myocardial infarction. He took TP 93-G for 5 days and the symptoms disappeared.

Example 11

A 79-year-old male was hospitalized, the diagnosis indicating interior and posterior myocardial infarction and a 25% disorder of the heart. His blood pressure was 130 over 70 and he had severe arrhythmia, as well as ventricular premature contractions (VPC). He was treated with TP 93-G and, after 46 days, the VPC and arrhythmia disappeared.

Example 12

A 63-year-old male suffered from fatigue, heart palpitations and shortness of breath. He had atrial fibrillation (AF) (190 pulses per minute) and one premature ventricular contraction (PVC) per minute as observed via an electrocardiogram. The hospital diagnosis indicated myocardial infarction. After taking TP 93-G for 21 days, both the PVC and AF on the electrocardiogram disappeared.

Example 13

A 61-year-old female had a rapid pulse, heart palpitations and difficulty breathing for more than 8 years. After daily treatment with TP 93-G for 4 months, the symptoms disappeared.

Example 14

A 63-year-old female had a slow pulse rate (40–52) and myocardial infarction. After 5 months of treatment with TP 93-G, the symptoms disappeared.

Example 15

A 62-year-old male was in bed for 2 years due to myocardial infarction. After taking TP 93-G for 1 month, he was able to return to work and resume his daily activities.

Example 16

A 62-year-old male had cerebral infarction. He had numbness on the left side of his body. After taking TP-93G for 1 month, the numbness eased substantially and disappeared completely after 6 months of treatment.

Example 17

A 76-year-old female had a moderate form of Alzheimer's disease. She had a heart condition, fluctuation in her blood pressure, a bladder condition, frequent diarrhea, a poor appetite and got lost on public streets. After treatment with TP 93-G for 4 months, the patient stopped getting lost on public streets and her blood pressure stabilized.

Example 18

An 89-year-old male had a severe brain disorder. He was not able to recognize his close relatives and got lost in the street. He is now undergoing treatment with TP 93-U.

Example 19

The sister-in-law of the primary inventor suffered from chronic depression. Recently, the symptoms intensified. After treatment with TP 93-G for 4 days, the depression disappeared.

Example 20

The co-inventor's brother, age 42, had arrhythmia for at least 5 years. Since treatment with TP 93-PI 4 months ago, the symptoms have not recurred.

We claim:

1. A pharmaceutical composition in unit dosage form suitable for the treatment of a condition selected from the group consisting of cardiovascular disease and cerebrovascular disease comprising a therapeutically effective amount of a member selected from the group consisting of:

I. a mixture of aqueous extracts of:
   a. root tissue of the plant *Asparagus cochinchinensis* containing asparagine, β-sitosterol and 5-methoxymethylfurfural,
   b. root tissue of the plant *Ophiopogon japonicus* containing glucose, starch, vitamin A and β-sitosterol,
   c. root tissue of the plant *Salvia miltiorrhiza* containing tanshinone A $C_{18}H_{12}O_3$, tanshinone B $C_{19}H_{18}O_3$ and tanshinone C $C_{19}H_{20}O_3$,
   d. root tissue of the plant *Angelica aeutiloba kitagawa* containing ligustillide,
   e. root tissue of the plant *Rehmannia glutinosa Liboschitz* containing rehmannin, xylitol, glucose, mannitol, iron, vitamin A and catalpol,
   f. white stone-like material formed by bacteria on surface of underground root of tree *Poria cocos wolf* containing ergosterol,
   g. ripe fruits of the plant *Schizandra chinensis* containing citral, schizandrin $C_{23}H_{32}O_6$, vitamin A, vitamin C and d-ylangene,
   h. root tissue of the plant *Platycodon grandiflorum* containing polygalacic acid platycoside, inulin and phytosterol,
   i. root tissue of the plant *Polygala tenuifolia* containing tenuifolin, polygallitol $C_6H_{12}O_5$ and onsicin $C_{24}H_{47}O_5$,
   j. dried seeds of the plant *Zizyphus jujuba* containing betulinic acid $C_{30}H_{48}O_3$, betulin $C_{30}H_{50}O_2$, β-sitosterol, fatty acids, vitamin A and organic acids,
   k. dried seeds of the plant *Biota orientalis* containing borneol and fatty acids,
   1. root tissue of the plant *Pueraria pseudo-hirsuta* containing flavon, puerarin and daidzein, m. root tissue of the plant *Panax ginseng* containing ginsenoside, panacene $C_{15}H_{24}$, panaquilon $C_{32}H_{56}O_{14}$, panaxin $C_{23}H_{38}O_{10}$, organic acids, vitamin A, vitamin $B_1$, vitamin $B_2$, vitamin C, inorganic salts and starch, n. root tissue of the plant *Codonopsis pilosula* containing alkaloid, saponin, protein, starch, vitamin $B_1$ and vitamin $B_2$, o. root tissue of the plant *Scrophularia ningpoensis* containing harpagide, phytosterol, linoleic acid and alkaloid, p. root tissue of the plant *Glycyrrhiza uralensis* containing glycyrrhizic acid, calcium salt, potassium salt, glycyrrhizin, glycyrrhizic acid, liquiritigenin $C_{21}H_{22}O_9$, glucose, mannitol, malic acid and l-asparagine, q. root tissue of the plant *Panax pseudo-ginseng* containing pseudo-ginseng A $C_{30}H_{52}O_{10}$, pseudo-ginseng B $C_{23}H_{38}O_{10}$ and flavon, r. the whole plant *Ganoderma japonicum* containing amino acid, protein, sterol and alkaloid, s. root tissue of the plant *Coptis chinensis* containing berberine $C_{20}H_{19}O_5N$, coptisine $C_{19}H_{15}O_5N$, palmatine $C_{21}H_{23}O_5N$ and woorenine $C_{20}H_{17}O_5N$, t. flower heads of the plant *Chrysanthemum morifolium* containing adenine $C_5H_5N_5$, stachydrine $C_7H_{13}NO$, choline and oil, and u. skins of the plant *Phellodendron amurense* containing berberine, obakunone $C_{26}H_{30}O_7$, obakulactone $C_{26}H_{30}O_8$ and dictammolactone $C_{28}H_{30}O_9$;

II. a mixture of the aqueous extracts of:
 I.a.,
 I.b.,
 I.c.,
 I.d.,
 I.e.,
 I.f.,
 I.g.,
 I.h.,
 I.i.,
 I.k.,
 I.l.,
 I.m.,
 I.n.,
 I.o.,
 I.p.,
 I.q., and
 I.r.;

III. a mixture of the aqueous extracts of:
 I.a.,
 I.b.,
 I.c.,
 I.d.,
 I.e.,
 I.f.,
 I.g.,
 I.h.,
 I.i.,
 I.k.,
 I.l.,
 I.m.,
 I.o.,
 I.p.,
 I.r.,
 I.s.,
 I.t.; and IV. a mixture of finely divided:

1. root tissue of the plant *Salvia miltiorrhiza* containing tanshinone A $C_{18}H_{12}O_3$, tanshinone B $C_{19}H_{18}O_3$ and tanshinone C $C_{19}H_{20}O_3$, 2. root tissue of the plant *Panax pseudo-ginseng* containing ginsenoside, panacene $C_{15}H_{24}$, panaquilon $C_{32}H_{56}O_{14}$, panaxin $C_{23}H_{38}O_{10}$, organic acids, vitamin A, vitamin $B_1$, vitamin $B_2$, vitamin C, inorganic salts and starch, 3. root tissue of the plant *Red ginseng* containing ginsenoside, panacene $C_{15}H_{24}$, panaquilon $C_{32}J_{56}o_{14}$, panaxin $C_{23}H_{38}O_{10}$, organic acids, vitamin A, vitamin $B_1$, vitamin $B_2$, vitamin C, inorganic salts and starch, and 4. Amber, a hard translucent fossil resin buried between roots of old trees, containing succinoabietinolic acid $C_{40}H_{60}O_5$, succinogiluinic acid $C_{24}C_{36}O_2$, succinoresinol, succinoabietinol $C_{40}H_{60}O$ and fatty acids, wherein, in composition I, the weight percentage of each plant tissue, based on the total weight of said plants from which said mixture of aqueous extracts is derived, is in the range of:

from about 5% to about 20% of a.;
from about 5% to about 20% of b.;
from about 5% to about 20% of c.;
from about 5% to about 20% of d.;
from about 5% to about 20% of e.;
from about 5% to about 16% of f.;
from about 1% to about 15% of g.;
from about 1% to about 6% of h.;
from about 1% to about 10% of i.;
from about 1% to about 10% of j.;
from about 1% to about 10% of k.;
from about 1% to about 10% of l.;
from about 1% to about 10% of m.;
from about 1% to about 20% of n.;
from about 1% to about 15% of o.;
from about 0.1% to about 2% of p.;
from about 1% to about 15% of q.;
from about 1% to about 10% of r.;
from about 1% to about 5% of s.;
from about 1% to about 10% of t.; and
from about 1% to about 10% of u.;

wherein, in composition II, the weight percentage of each plant tissue, based on the total weight of said plants from which said mixture of aqueous extracts is derived, is in the range of:

from about 3% to about 15% of a.;
from about 3% to about 15% of b.;
from about 5% to about 20% of c.;
from about 3% to about 15% of d.;
from about 5% to about 20% of e.;
from about 5% to about 20% of f.;
from about 2% to about 15% of g.;
from about 1% to about 5% of h.;
from about 2% to about 15% of i.;
from about 2% to about 15% of j.;
from about 2% to about 5% of k.;
from about 2% to about 15% of l.;
from about 1% to about 10% of m.;
from about 2% to about 15% of n.;

from about 3% to about 15% of o.;
from about 0.1% to about 2% of p.;
from about 3% to about 15% of q.; and
from about 3% to about 15% of r.;
wherein, in composition III, the weight percentage of each plant tissue, based on the total weight of said plants from which said mixture of aqueous extracts is derived, is in the range of:
from about 5% to about 20% of a.;
from about 2% to about 10% of b.;
from about 2% to about 10% of c.;
from about 2% to about 10% of d.;
from about 2% to about 10% of e.;
from about 2% to about 10% of f.;
from about 2% to about 10% of g.;
from about 2% to about 4% of h.;
from about 2% to about 10% of i.;
from about 2% to about 10% of j.;
from about 1% to about 5% of k.;
from about 2% to about 10% of l.;
from about 2% to about 8% of m.;
from about 2% to about 15% of o.;
from about 0.1% to about 2% of p.;
from about 2% to about 10% of r.;
from about 1% to about 5% of s.; and
from about 1% to about 5% of t.;
and wherein, in composition IV, the weight percentage of each plant tissue, based on the total weight of said plants from which said mixture of finely divided tissue is derived, is in the range of:
from about 20% to about 60% of 1.;
from about 20% to about 60% of 2.;
from about 10% to about 30% of 3.; and
from about 5% to about 20% of 4.

2. A method for treating a patient in need thereof comprising administering thereto a therapeutic amount of a pharmaceutical composition of claim 1 effective to prevent or ameliorate the effects of a condition selected from the group consisting of cardiovascular disease, cerebrovascular disease, Alzheimer's disease, depression and combinations thereof.

3. The method of claim 2 wherein the amount of composition I administered is in the range of from about 150 to about 600 mg/kg of body weight of said patient.

4. The method of claim 2 wherein the amount of composition II administered is in the range of from about 100 to about 400 mg/kg of body weight of said patient.

5. The method of claim 2 wherein the amount of composition III administered is in the range of from about 80 to about 300 mg/kg of body weight of said patient.

6. The pharmaceutical composition I of claim 1 wherein the weight ratio of water to said plant tissues in the range of from about 2:1 to about 10:1.

7. The pharmaceutical composition II of claim 1 wherein the weight ratio of water to said plant tissues in the range of from about 2:1 to about 10:1.

8. The pharmaceutical composition III of claim 1 wherein the weight ratio of water to said plant tissues in the range of from about 2:1 to about 10:1.

9. The pharmaceutical composition I, II or III of claim 1 wherein said composition is in a parenterally injectable form.

10. The pharmaceutical composition of claim 1 in an orally administrable form.

11. The pharmaceutical composition I, II or III of claim 1 wherein said composition is in an infusible form.

12. The pharmaceutical composition I, II or III of claim 1 in powder form prepared by removing water therefrom.

13. The pharmaceutical composition of claim 1 or 12 in unit dosage form comprising said powder or finely divided tissue in tablet or capsule form.

14. The pharmaceutical composition of claim 1 or 13 wherein the weight percentage of extracted plant material or finely divided tissue to non-plant material is in the range of from about 70% to about 95%.

15. A method of preparing the pharmaceutical compositions I, II or III of claim 1 comprising extracting the water-soluble components from the tissue of said plants with an aqueous medium.

16. The method of claim 15 wherein the weight ratio of said aqueous medium to said plant tissues is from about 5:1 to about 20:1.

17. The method of claim 15 wherein said extraction is carried out by boiling said plant tissues in said aqueous medium.

18. The method of claim 17 wherein said boiling is carried out for a period of time of from about 0.5 hr. to about 4 hr.

19. The method of claim 15 wherein, following said extraction, the amount of water in said aqueous extract is reduced.

20. The method of claim 19 wherein the amount of water in said aqueous extract is reduced such that the weight ratio of water to extracted material from said plant tissues is from about 5:1 to about 30:1.

21. The method of claim 19 wherein the amount of water in said aqueous extract is reduced by boiling.

22. The method of claim 15 including the step of removing water-insoluble material from said aqueous extract following said extraction.

23. The method of claim 22 wherein said water-insoluble material is removed from said aqueous extract by filtration.

24. The method of claim 22 including the step, following separation of said water-insoluble material, of removing unwanted impurities from said aqueous filtrate.

25. The method of claim 24 wherein said impurities are removed from said aqueous extract by a chromatographic technique.

26. A method of preparing the pharmaceutical composition IV of claim 1 comprising grinding said tissues to a finely divided state.

27. The method of claim 26 including the step of intimately admixing said ground tissue to produce a substantially homogeneous mixture thereof.

28. A health drink suitable for administration to a patient in need of treatment of cardiovascular disease, cerebrovascular disease, Alzheimer's disease, depression and combinations thereof comprising an enterally administrable solution of the composition of claim 12.

29. The health drink of claim 23 additionally containing health drink adjuvants.

30. A health drink suitable for administration to a patient in need of treatment of cardiovascular disease, cerebrovascular disease, Alzheimer's disease, depression and combinations thereof comprising an enterally administrable solution of a powder prepared by extracting the water-soluble components from composition IV of claim 1 with an aqueous medium followed by removing water from said aqueous medium containing said extracted water-soluble components.

31. The health drink of claim 30 additionally containing health drink adjuvants.

32. The method of claim 2 wherein the amount of composition IV administered is in the range of from about 20 to about 100 mg/kg of body weight of said patient.

33. The method of claim 2 wherein said composition I, II or III is administered orally, parenterally or by infusion.

34. The method of claim 2 wherein said composition IV is administered orally.

35. A method for treating a patient in need thereof comprising administering thereto a therapeutic amount of the pharmaceutical composition of claim 12 or 13 effective to prevent or ameliorate the effects of a condition selected from the group consisting of cardiovascular disease, cerebrovascular disease, Alzheimer's disease, depression and combinations thereof.

* * * * *

UNITED STATES PATENT AND TRADEMARK OFFICE
CERTIFICATE OF CORRECTION

PATENT NO. : 5,589,182
DATED : December 31, 1996
INVENTOR(S) : RENKI TASHIRO, ET AL It is certified that error appears in the above-identified patent and that said Letters Patent is hereby corrected as shown below:

In column 21, line 40, insert the following between "I.i." and "I.k.":  -- I.j., --

In column 21, line 58, insert the following between "I.i." and "I.k.":  -- I.j., --

In column 22, lines 10-11, change "$C_{32}J_{56}O_{14}$" to -- $C_{32}H_{56}O_{14}$ --

Signed and Sealed this

Eighth Day of April, 1997

Attest:

BRUCE LEHMAN

Attesting Officer

Commissioner of Patents and Trademarks